United States Patent [19]

Ueda et al.

[11] Patent Number: 4,937,386
[45] Date of Patent: Jun. 26, 1990

[54] 4,4,5-TRIMETHYL-2-(2-NITRO-4-METHYL-SULFONYLBENZOYL) CYCLOHEXANE-1,3-DIONE

[75] Inventors: Akiyoshi Ueda; Hideo Hosaka, both of Odawara, Japan

[73] Assignee: Nippon Soda Co., Ltd., Tokyo, Japan

[21] Appl. No.: 373,446

[22] Filed: Jun. 30, 1989

[30] Foreign Application Priority Data

Jul. 7, 1988 [JP] Japan ................... 63-167739

[51] Int. Cl.$^5$ ........................................... C07C 147/00
[52] U.S. Cl. ........................................ 568/31; 71/103
[58] Field of Search ...................... 71/103; 568/31; 260/465

[56] References Cited

FOREIGN PATENT DOCUMENTS 0186118  2/1986  European Pat. Off. ............ 260/465
0186119  2/1986  European Pat. Off. ............ 260/465

*Primary Examiner*—Anton H. Sutto
*Assistant Examiner*—Deborah D. Carr
*Attorney, Agent, or Firm*—George B. Oujevolk

[57] ABSTRACT

The present invention relates to 4,4,5-trimethyl-2-(2-nitro-4-methylsulfonylbenzoyl) cyclohexane-1,3-dione which is useful as herbicide.

2 Claims, No Drawings

4,4,5-TRIMETHYL-2-(2-NITRO-4-METHYLSULFONYLBENZOYL) CYCLOHEXANE-1,3-DIONE

The present invention relates to 4,4,5-trimethyl-2-(2-nitro-4-methylsulfonyl)benzoyl cyclohexane-1,3-dione, herbicidal compositions in the form of mixture of such compound with inert carrier(s), and a process for the production of such compound.

In many cases of agricultural or horticultural cultivation, a lot of kinds and amount of herbicides have come to be used for the weed control in order to save the labors consuming for removing weeds in the fields, however, in some occasion, phytotoxicity of herbicides may injure crops, or herbicides remaining in the field may cause environmental pollution.

Consequently, chemicals possessing the excellent efficacy and the higher safety to mammal have been awaited to be developed.

The compound of this invention is included in the claims of EP-186118, but is not mentioned at all in the description.

An object of the present invention is to provide a herbicide which is synthesized advantageously in an industrial scale, gives sure effect at a lower dosage, is highly safety and has good selectivity for crops.

According to the first aspect of the present invention, there is provided 4,4,5-trimethyl-2-(2-nitro-4-methylsulfonylbenzoyl)cyclohexane-1,3-dione (I).

According to the second aspect of the present invention, there is provided a herbicidal composition comprising an inert carrier and an effective amount of the compound (I).

The compound (I) shows higher herbicidal activity against a wide range of weeds including Graminea weeds, Cyperacea weeds and broad-leaved weeds than known compounds shown in the patent mentioned above. Furthermore, the compound (I) shows excellent selectivity to corn in comparison to known compounds mentioned above.

According to a third aspect of the present invention, there is provided a process for the preparation of the compound (I), comprising the step of reaction as illustrated by the following equation.

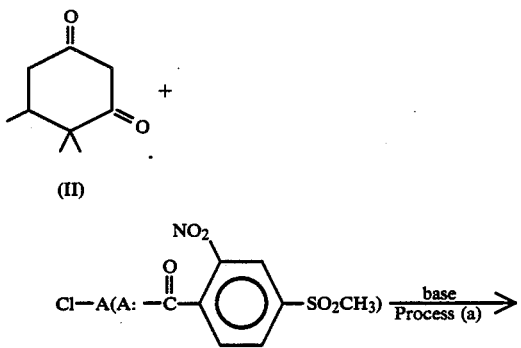

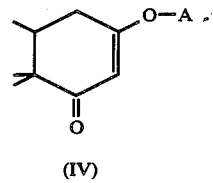

(IV)

or

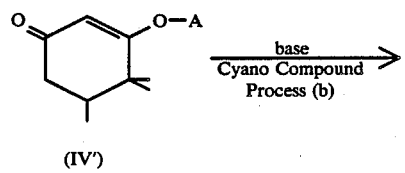

(IV')

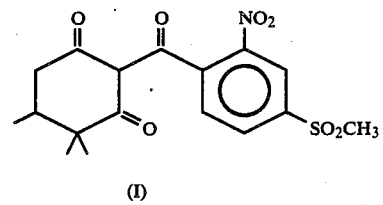

(I)

A base used in Process (a) includes an alkali metal hydroxide such as KOH or NaOH, a hydroxide of alkaline earth metal, tri ($C_{1-6}$ alkyl) amine, pyridine, sodium carbonate, and sodium phosphate. A mole of each of compound (II) and compound (III) is used together with a mole or excessive amount of base. A solvent used includes water, methylene chloride, toluene, ethyl acetate, dimethylformamide, THF, dimethoxyethane, and acetonitrile. The reaction mixture is stirred at 0° C. to 50° C. until the reaction is completed. The reaction mixture is treated by an ordinary method.

In Process (b), one mole of compound (IV) is reacted with 1 to 4 moles, preferably 2 moles, of base and an amount from 0.01 to 0.5 moles or more, preferably 0.1 moles, of cyano compound. Any of the bases listed in Process (a) is applicable to this process. A cyano compound used includes potassium cyanide, acetone cyanohydrin and hydrogen cyanide.

The addition of a small amount of phase-transfer catalyst such as crown ether results in the completion of the reaction in a shorter time.

The reaction mixture is stirred until the completion of the rearrangement reaction at a temperature lower than 80° C., preferably 20° C. to 40° C. A solvent used includes 1,2-dichloroethane, toluene, acetonitrile, methylene chloride, ethyl acetate, dimethylformamide, methylisobutylketone, THF, and dimethoxyethane.

The material compound represented by the formula (II) and the compound of the present invention have the following tautomer(s) respectively. The following structural formulae are illustrated with omission of substituents on the benzene ring.

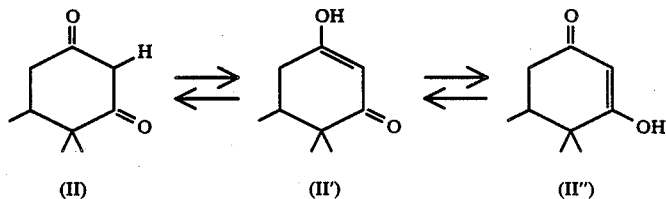

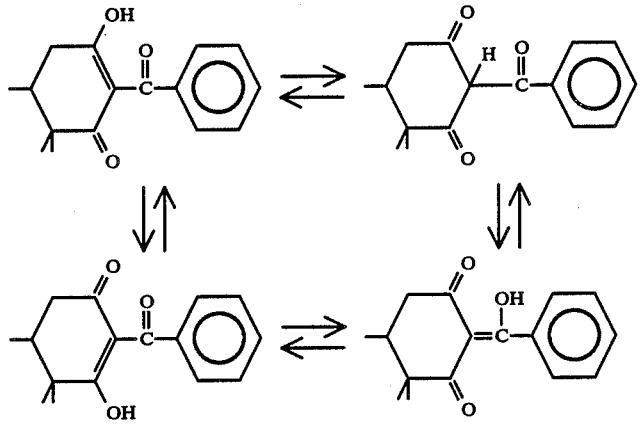

The intended product can be obtained by carrying out a usual aftertreatment after the reaction is completed. The strusture of the compound of this invention has been determined by means of IR, NMR, MASS spectrum, etc.

The following Examples illustrate the invention.

EXAMPLE 1

4,4,5-Trimethyl-2-(2-nitro-4-methylsulfonylbenzoyl)cyclohexane-1,3-dione 4,4,5-trimethyl-cyclohexane-1,3-dione (0.98 g, 6.36 mmole) and triethylamine (0.77 g, 7.26 mmole) were dissolved in methylene chloride (30 ml). Into the resulting solution cooled with ice, a methylene chloride solution (5 ml) of 2-nitro-4-methylsulfonylbenzoyl chloride (1.68 g, 6.38 mmole) was dropped, and then this solution was stirred at room temperature for an hour. The resulting solution was washed with water, dried with anhydrous magnesium sulfate, and concentrated under reduced pressure. The residue was dissolved in acetonitrile (40 ml), into which triethylamine (0.77 g, 7.62 mmole) and potassium cyanide (0.1 g, 1.54 mmole) were added to stir at room temperature for 16 hours. The reaction solution was concentrated under reduced pressure. The residue was dissolved by adding ethyl acetate and water. To the resulting solution, diluted hydrochloric acid was added until the aqueous layer became acidic (pH 2 or below). The organic layer was washed with water, dried with anhydrous magnesium sulfate and concentrated under reduced pressure. Methanol was added to the residue to crystallize to give crystal (0.57 g, mp: 166°–7° C.).

As mentioned previously, the compounds possess superior herbicidal activity. The compounds may be applied directly to the soil as preemergence treatment or to plant foliage as post-emergence treatment, or they can be mixed intimately with soil. The compounds may be applied to soil or to plant foliage in amount of 1 g or more per 10 are.

A herbicidal composition having a compound of this invention as its active ingredient may be formulated by mixing suitable carriers in a form generally used in agricultural chemicals such as wettable powder, water soluble powder, granule, emulsifiable concentrate and flowable. As solid carriers, talc, white carbon, bentonite, clay, diatomaceous earth or the like may be used. As liquid carriers, water, alcohol, benzene, xylene, kerosene, mineral oil, cyclohexane, cyclohexanone, dimethylformamide or the like may be used. A surface active agent may, if necessary, be added in order to give a homogeneous and stable formulation.

Compounds can also be applied admixed with other chemicals, which are used in agronomic and horticultural management and which are compatible with such compounds. Such chemicals can be, but are not restricted to, the classes of chemical commonly known as fungicides, insecticides, acaricides, herbicides and plant growth regulators. In particular, by mixing it with the other herbicides, its applied dosage and manpower can be decreased and furthermore, the higher effect by synergetic function of both chemicals can be expected.

For admixture of the compound with known herbicides, the use is recomended of benthiocarb, molinate, dimepiperate or other carbamate-type herbicides; thiocarbamate-type herbicides; butachlor, pretilachlor, mefenacet or other acid amide-type herbicides; chlormethoxynil, bifenox or other diphenylether-type herbicides; pyrazolate, atrazine, cyanazine or other triazine-type herbicides; chlorsulfuron, sulfometuron-methyl or other sulfonylurea-type herbicides; MCP, MCPB or other phenoxy alkane carboxylic acid-type herbicides; diclofop-methyl or other phenoxy propionic acid-type herbicides; fluazifopbutyl or other pyridyloxyphenoxypropionic acid-type herbicides; benzoylprop-ethyl, flamprop-ethyl or other benzoylaminopropionic acid-type herbicides; and, as others, piperophos, dymron, bentazon, difenzoquart, naproanilid, HW-52 (4-ethoxy methoxy benzo-2',3'-dichloroanilide), KNW-242 (1-(3-methylphenyl)-5-phenyl-1H-1,2,4-triazole-3-carboxamide), quinclorac (3,7-dichloro-8-quinoline carboxylic acid), and further, sethoxydim, alloxydim-sodium and other cyclohexanedione-type herbicides. These herbicides in various combinations may also be mixed with a vegetable oil or an oil concentrate.

The concentration of the active ingredient in a herbicidal composition may vary according to type of formulation, and the concentration is, for example, in the range of 5–70 weight percent, preferably 10–30 weight percent, in wettable powder; 3–70 weight percent, preferably 5–20 weight percent, in emulsifiable concentrate; 0.01–30 weight percent, preferably 0.05–10 weight percent, in granule.

A wettable powder, or an emulsifiable concentrate thus produced may be diluted with water to a specified concentration and used as a liquid suspension or a liquid emulsion for treating soils or plant foliage. Further, a granule may be directly used for soil or foliage treatment.

Non-limiting examples of herbicidal composition are illustrated by the following Examples:

EXAMPLE 2

Wettable powder

|  | parts by weight |
| --- | --- |
| Compound (I) | 20 |
| White carbon | 20 |
| Diatomaceous earth | 52 |
| Sodium alkylsulfate | 8 |

These are mixed homogeneously and reduced to fine particles to provide a wettable powder containing 20% of active ingredient. In use, it is diluted to a desired concentration with water, and is sprayed as suspension.

EXAMPLE 3

Emulsifiable concentrate

|  | parts by weight |
| --- | --- |
| Compound (I) | 20 |
| xylene | 55 |
| Dimethylformamide | 15 |
| polyoxyethylene phenyl ether | 10 |

These are mixed and dissolved to provide an emulsifiable concentrate containing 20% of active ingredient. In use, it is diluted to a desired concentration with water, and sprayed as an emulsion.

EXAMPLE 4

Granule

|  | Parts by weight |
| --- | --- |
| Compound (I) | 5 |
| Talc | 40 |
| Clay | 38 |
| Bentonite | 10 |
| Sodium alkyl sulfate | 7 |

These are mixed homogeneously to provide a granule containing 5% of active ingredient.

The herbicidal effects of compounds are illustrated by the following tests:

TEST 1

Postemergence treatment test

Seeds of large crabgrass, redroot pigweed, rice flatsedge, velvetleaf and corn were planted in clay pots (12 cm depth and 16 cm diameter) containing clay loam soil and were allowed to grow in greenhouse. When the plants were grown to a 5–10 cm height, aqueous suspensions, prepared by diluting an emulsifiable concentrate with water to specified concentration (250 ppm), were sprayed on the foliage of the plants at a rate of 100 1/10a by using a micro-sprayer.

Three weeks after treatment, the degree of damage of the each plants was observed and evaluated on the scale of value of 0–10, which has the following meanings.

| Index | Degree of damage |
| --- | --- |
| 0 | 0% |
| 2 | 20–29% |
| 4 | 40–49% |
| 6 | 60–69% |
| 8 | 80–89% |
| 10 | 100 |

Index 1, 3, 5, 7 and 9 mean the intermediate degree between 0 and 2, 2 and 4, 4 and 6, 6 and 8, 8 and 10 respectively.

Degree of damage (%) =

$$\frac{\left(\begin{array}{c}\text{Fresh weight}\\\text{in untreated plot}\end{array}\right)-\left(\begin{array}{c}\text{Fresh weight}\\\text{in treated plot}\end{array}\right)}{\text{Fresh weight in untreated plot}} \times 100$$

The results are shown in Table 1

TABLE 1

| Compound No. | Application Rate of Active Ingredient (g/10 a) | Degree of damage (Index) | | | | |
| --- | --- | --- | --- | --- | --- | --- |
| | | corn | large crab-grass | redroot piyweed | rice flats-edge | velvet-leaf |
| Compound (I) | 25 | 0 | 10 | 10 | 10 | 10 |
| *Comparative compound | 25 | 7 | 9 | 5 | 8 | 8 |

*Comparative Compound 4,4,6-trimethyl-2-(2-nitro-4-methylsulfonylbenzoyl)-cyclohexane-1,3-dione (shown in EP186118)

What we claim is:

1. A process for the preparation of 4,4,5-trimethyl-2-(2-nitro-4-methylsulfonylbenzoyl)cyclohexane-1,3-dione which comprises that 4,4,5-trimethylcyclohexane-1,3-dione and 2-nitro-4-methylsulfonylbenzoyl chloride are reacted in the presence of a base, and the obtained product undergoes a rearrangement reaction in the presence of a base and a cyano compound.

2. A herbicidal composition, comprising an inert carrier and a selectively effective amount of 4,4,5-Trimethyl-2-(2-nitro-4-methylsulfonylbenzoyl)cyclohexane-1,3-dione which is particularly useful in protecting corn against crabgrass, redroot pigweed, rice flatsedge and similar weeds which attack corn.

* * * * *